United States Patent
Aida et al.

(10) Patent No.: US 6,441,259 B1
(45) Date of Patent: Aug. 27, 2002

(54) PROCESS FOR THE CONTINUOUS PREPARATION OF TETRACYCLODODECENS

(75) Inventors: Fuyuki Aida, Kanagawa; Takashi Suzuki, Chiba; Yasuo Matsumura, Kanagawa, all of (JP)

(73) Assignee: Nippon Petrochemicals Co., Ltd., Tokyo (JP)

( * ) Notice: Subject to any disclaimer, the term of this patent is extended or adjusted under 35 U.S.C. 154(b) by 0 days.

(21) Appl. No.: 09/869,776

(22) PCT Filed: Nov. 10, 2000

(86) PCT No.: PCT/JP00/07934

§ 371 (c)(1),
(2), (4) Date: Jul. 5, 2001

(87) PCT Pub. No.: WO01/34540

PCT Pub. Date: May 17, 2001

(30) Foreign Application Priority Data

Nov. 10, 1999 (JP) .............................. 11-319710
Nov. 10, 1999 (JP) .............................. 11-319711
Nov. 10, 1999 (JP) .............................. 11-319714

(51) Int. Cl.[7] .............................................. C07C 13/28
(52) U.S. Cl. ...................... 585/360; 585/361; 585/362; 585/350
(58) Field of Search ................. 585/360, 361, 585/362, 350

(56) References Cited

U.S. PATENT DOCUMENTS 4,320,239 A * 3/1982 Schneider

FOREIGN PATENT DOCUMENTS

| JP | 3128333 | * | 5/1991 |
| JP | 3-128333 A1 | | 5/1991 |
| JP | 6-9437 A1 | | 1/1994 |
| JP | 06072909 | * | 3/1994 |
| JP | 10-287592 A1 | | 10/1998 |
| WO | WO 00/01742 A1 | | 1/2000 |

* cited by examiner

Primary Examiner—Paul J. Killos
Assistant Examiner—Hector Reyes
(74) Attorney, Agent, or Firm—Weingarten, Schurgin, Gagnebin & Lebovici LLP (57) ABSTRACT

The present invention relates to a process for the preparation of highly purified tetracyclododecenes, which can be a raw material of cycloolefin (co)polymers possessing excellent characters concerning their optical property, high transparency, heat resistance, and oil absorbency, from an inexpensive raw material of crude DCPD in a stable, continuous, and longstanding process. In the continuous preparation of tetracyclododecenes described in the present invention, it is possible to employ crude dicyclopentadiene, that is, dicyclopentadiene having low purity, as a raw material. It is also possible to produce highly purified tetracyclododecenes by maintaining the ratios of one, two, or three compounds selected from the group comprising isoprene, piperylene, and 1-methyl-2-norbornenes shown by the general formula (4) against the sum of dicyclopentadiene and cyclopentadiene within the specified ranges, wherein all these substances are contained in the raw material that are fed into a reactor.

6 Claims, 1 Drawing Sheet

Fig. 1

PROCESS FOR THE CONTINUOUS PREPARATION OF TETRACYCLODODECENS

FIELD OF THE INVENTION

The present invention relates to a process for the continuous preparation of tetracyclododecenes, more particularly, the invention relates to a process for preparing tetracyclododecenes (may be abbreviated hereafter as TCD), which can be a raw material of cycloolefin (co)polymers possessing excellent characters concerning their optical property, high transparency, heat resistance, and oil absorbency, from an inexpensive raw material of crude dicyclopentadiene (DCPD) in a stable, continuous, and longstanding process.

BACKGROUND ART

Cycloolefin (co)polymers are the focus of industrial attention as polymers that possess excellent characters concerning their optical property, high transparency, heat resistance, and oil absorbency. Cycloolefins represented by cyclohexene, dicyclopentadiene (may be abbreviated hereafter as DCPD), norbornenes, and tetracyclododecenes are a useful raw material for the polymer. These cycloolefins are generally prepared using organometallic complex catalysts. The polymerization method is roughly classified into two: one is the single polymerization of cycloolefins polymerized at their olefinic site or the copolymerization with lower alpha-olefins using Ziegler catalysts or metallocene catalysts. The other is known as the metathesis polymerization that employs the carbene-type catalysts.

With regard to the preparative method of TCD, a typical method is mixing cyclopentadiene (may be called CPD hereafter), dicyclopendtadiene (may be called DCPD hereafter), or a mixture thereof, with 2-norbornenes and ethylene, in a heated condition for the Diels-Alder reaction. This yields a reaction mixture containing tetracyclododecenes and 2-norbornenes. The process of recovery and circulation of norbornenes from the reaction mixture follows. A method of preparing tetracyclododecenes accompanied with the processes of recovery and circulative re-use of the generated norbornenes is reported, for example, in Japan Open H06-9437. This patent proposes a use of DCPD of high purity as a raw material, because industrially available crude DCPD contains impurities such as propenylnorbornene, isopropenylnorbornene, vinylnorbornene, methylbicyclononadiene, or methyldicyclopentadiene. In said process, the reaction mixture discharged from a reactor after the reaction is cooled, depressurized, and treated for separation. The low boiling component in the reaction mixture such ethylene is removed in said process. However, the raw material DCPD of high purity mentioned in the above patent is naturally associated with the high cost for the raw material. Even in the use of highly purified DCPD, a removing process of the low-boiling component is required for the effective use of unreacted compounds. This also leads to the high cost for the raw materials, therefore, rarely adopted in the industrial production.

It is thus concluded that the use of inexpensive crude DCPD as a raw material, and the recovery and circulative re-use of the unreacted olefin leads to an inexpensive production method of TCD, and thus is preferred. However, impurities in the crude DCPD cause newly generation of low-molecular compounds such as isoprene, piperylene, and 1-methyl-2-norbornene. They may contaminate the recovered and circulated raw materials, and prevent a stable production of TCD. Besides, the present inventors discovered that the by-produced high boiling compounds might degrade the purity of the final product TCD. It is also worried that the generated isoprene, piperylene, and 1-methyl-2-norbornene may be accumulated in the circulating system and, in extreme cases, may cause inability to continue the operation, as they are estimated to come from the crude DCPD, which is continuously fed into the reaction system. The present invention proposes a production method of tetracyclododecenes using inexpensive crude DCPD as a raw material in a stable and continuous process.

DISCLOSURE OF THE INVENTION

The first item of the present invention relates to a continuous method for the production of tetracyclododecenes shown by the general formula (3), characterized by feeding continuously an olefin shown by the general formula (1), cyclopentadiene and/or dicyclopentadiene, and 2-norbornenes shown by the general formula (2), into a reaction vessel in heated state for the reaction, wherein at least a part of norbornenes and dicyclopentadiene contained in the reaction mixture coming from the reactor are circulated to said reactor, and relates to a continuous preparation of tetracyclododecenes characterized by maintaining one, two, or three compounds selected from the group comprising isoprene, piperylene, and 1-methyl-2-norbornene existent in the raw material introduced into the reactor within the range specified below Isoprene: 1–10,000 ppm(wt) against the sum of cyclopentadiene and dicyclopentadiene.

Piperylene: 1–10,000 ppm(wt) against the sum of cyclopentadiene and dicyclopentadiene. 1-Methyl-2-norbornenes shown by the general formula (4): 1–70,000 ppm(wt) against the sum of cyclopentadiene and dicyclopentadiene.

General formula (1)

General formula (2)

General formula (3)

General formula (4)

(R1 and R2 in these formulae are identical or different functional groups, and are a hydrogen atom, a methyl group, or an ethyl group).

The second item of the invention relates to a continuous production method of tetracyclododecenes shown by the general formula (3), characterized by inclusion of the following processes of 1 to 5, wherein the contents for one, two, or three compounds selected from the group comprising isoprene, piperylene, and 1-methyl-2-norbornene existent in the raw material introduced into the reactor are maintained within the range specified belolow.

Isoprene: 1–10,000 ppm(wt) against the sum of cyclopentadiene and dicyclopentadiene.

Piperylene: 1–10,000 ppm(wt) against the sum of cyclopentadiene and dicyclopentadiene.

1-Methyl-2-norbornenes shown by the general formula (4): 1–70,000 ppm(wt) against the sum of cyclopentadiene and dicyclopentadiene.

(where R1 and R2 in these formulae are identical or different functional groups, and are a hydrogen atom, a methyl group, or an ethyl group).

1) A process of feeding an olefin shown by the general formula (1), cyclopentadiene and/or dicyclopentadiene, and norbornenes shown by the general formula (2) into a reaction vessel continuously for the reaction (where R1 and R2 in these formulae are identical or different functional groups, and are a hydrogen atom, a methyl group, or an ethyl group).

General formula (1)

General formula (2)

General formula (3)

General formula (4)

2) A process of separating an olefin, cyclopentadiene and/or dicyclopentadiene, and norbornenes from the reaction mixture by distillation.

3) A process of circulating at least a part of an olefin, cyclopentadiene, and norbornenes respectively separated in said process 2 to the above reaction vessel.

4) A process of separating tetracyclododecenes from the reaction mixture by distillation succeeding said process 2.

5) A process of isolating tetracyclododecenes from the reaction mixture by distillation succeeding said process 4.

The third item of the invention relates to a continuous production of tetracyclododecenes described in the first item and the second item of the present invention, characterized by extracting dicyclopentadiene from the top of a distillation tower at a condition of the temperature and pressure of the distillation tower at the top in 50–120 degrees centigrade and less than 30 KPa, and the temperature and pressure at the bottom in 80–200 degrees and less than 80 KPa.

The fourth item of the invention relates to a continuous production of tetracyclododecenes described in the first item and the second item of the present invention, characterized by feeding an olefin, crude cyclopentadiene and/or cyclopentadiene, and norbornenes into a reaction vessel in heated sate for the reaction, at a condition of the reaction temperature in 100–400 degrees, the reaction pressure in 0.540 MPa, the residence time in 0.1–360 minutes, and in a molar ratio of dicyclopentadiene/olefin/norbornenes=1/(0.1–50)/(1–50), wherein 2 moles of cyclopentadiene is reduced to 1 mole of dicyclopentadiene.

According to the production methods described in the present invention, it is possible to produce highly purified tetracyclododecenes from a raw material of crude DCPD in a stable, continuous, and longstanding process. The detailed description of the invention is given hereafter.

In the production methods described in the present invention, the following reactions from 1 to 3 proceed at the continuous feed of an olefin, crude cyclopentadiene and/or dicyclopentadiene, and norbornenes into a reaction vessel in heated state for the reaction, that is,

1) The heat decomposition reaction of dicyclopentadiene to cyclopentadiene shown by the following equation (1) when the former is employed as a raw material.

Equation (1)

2) The formation reaction of norbornenes (may be called as alkyl-norbornenes hereafter) shown by the following equation (2) from an olefin and cyclopentadiene.

Equation (2)

3) The formation reaction of tetracyclododecenes (may be called as alkyl-tetracyclododecenes hereafter) shown by the following equation (3) from cyclopentadiene and norbornenes.

Equation (3)

The olefin employed in the present invention and shown by the general formula (1) is taken to mean olefins containing 2–4 carbon atoms. Typical examples of the olefin are ethylene, propylene, 1-butene, trans-2-butene, and cis-2-butene. It is preferred to employ the polymerization grade of them. Crude DCPD is used as a raw material in the present invention. The crude DCPD is obtained industrially at a low cost in a large quantity from the residue oils generated at the heat decomposition or the catalytic decomposition of light hydrocarbons like naphtha conducted for the purpose of producing lower olefin's such as ethylene. This is favorable for the purpose of the present invention. Crude DCPD having the purity in more than 70 wt % can be used. A more purified product, for example a product having the purity in 90–95 wt % or more, can be used as it is included in the crude product containing some impurities.

Examples of impurities existent in dicyclopentadiene are, as shown in the previous patent specification, propenylnorbornene, isopropenylnorbornene, vinylnorbornene, tetrahydromethylindene, and methyldicyclopentadiene. They may be contained depending on the quality of employed dicyclopentadiene up to 10% or a bit more in maximum.

The industrial production of cyclopentadiene depends on the heat decomposition of dicyclopentadiene. As the raw crude dicyclopentadiene contains impurities, the produced cyclopentadiene is also accompanied with impurities in the product. Such crude cyclopentadiene may by used as a raw material in the present invention favorably. Furthermore, CPD polymerizes easily to DCPD. Thus a mixture of crude CPD and crude DCPD may be included in the raw material according to the present invention. The purity of the above mixture is taken to mean the purity against the sum of CPD and DCPD.

Alkylnorbornenes are synthesized from the raw material comprising an olefin, cyclopentadiene and/or dicyclopentadiene at a temperature of 100–300 degrees and a pressure of 0.1–40 MPa. In a production method according to the present invention, it is possible to prepare alkyltetracyclododecenes and alkylnorbornenes simultaneously under the co-presence of an olefin and cyclopentadiene and/or dicyclopentadiene. In order to conduct the synthesis of tetracyclododecenes in an efficient manner, it is essential to make alkylnorbornenes coexist in the reaction system. Therefore the alkylnorbornenes separated from the reaction mixture after the reaction are circulated as a raw material for the re-use. Since alkylnorbornenes belong to compounds that are difficult to obtain industrially, it is essential for the preparation process according to the present invention to select a production condition, which facilitates the circulative use of alkylnorbornenes. For the purpose, it is necessary to select a condition. so that the amount of alkylnorbornenes generated in the reactor are larger than or equal to the amount of alkylnorbornenes consumed in the reaction system. Such conditions can be set, for instance, by adjusting a molar ratio of raw materials.

The raw material norbornenes in the present invention are taken to mean norbornenes shown by the general formula (2) (may be called as alkylnorbornenes hereafter), where R in the formula is a hydrogen atom or an alkyl group having the carbon number of one or two. They are precisely taken to mean 2-norbornene. 5-methyl-2-norbornene (methylnorbornene), 5-ethyl-2-norbornene (ethylnorbornene), and 5,6-dimethyl-2-norbornene (dimethylnorbornene). The isomeric form of these substituted compounds may be selected at will, that is, any isomer of them can be used for the purpose of the present invention.

The targeted product of tetracyclododecenes is taken to mean tetracyclododecenes (may be also called alkyltetracyclododecenes hereafter) shown by the general formula (3), where R in the formula is a hydrogen atom or an alkyl group having the carbon number of one or two. They are precisely taken to mean 1,4:5,8-dimethano-1,2,3,4,4a,5,8,8a-octahydronaphthalene (may be called as tetracyclododecene or TCD), 2-methyl-1,4:5,8-dimethano-1,2,3,4,4a,5,8,8a-octahydronaphthalene (methyltetracyclododecene), 2-ethyl-1,4,5,8-dimethano-1,2,3,4,4a,5,8,8a-octahydronaphthalene (ethyltetracyclododecene), and 2,3-dimethyl-1,4:5,8-dimethano-1,2,3,4,4a,5,8,8a-octahydronaphthalene (dimethyltetracyclododecene). The stereo chemistry of these compounds may be selected at will: any steric form for the substituents, any steric ring structure (such as the endo-exo form, the endo-endo form, the exo-endo form and the exo-exo form) may be included in the present invention.

Figure 1:
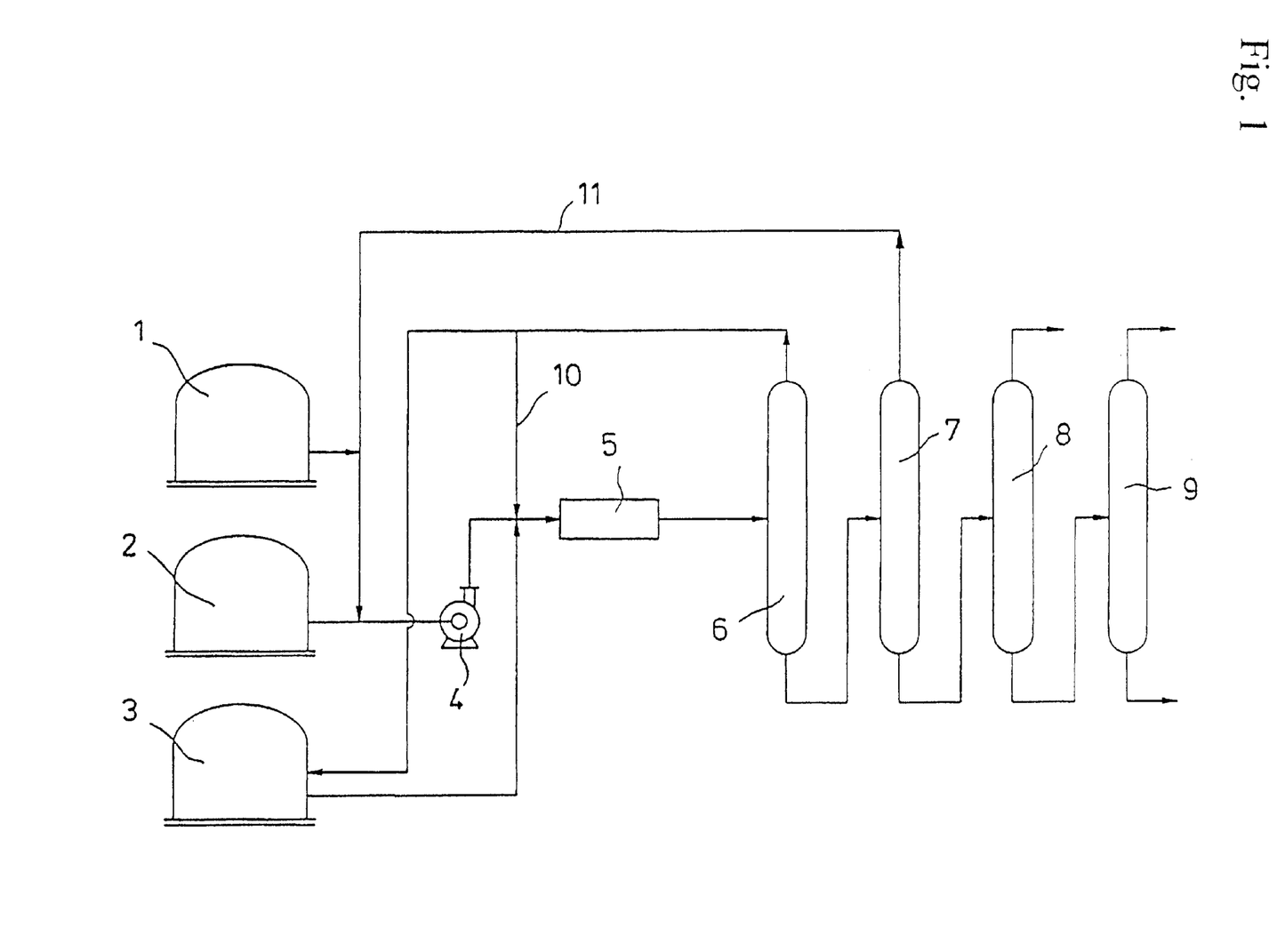

The detailed description of the present invention will be given hereafter depending on a figure. FIG. 1 illustrates a process flow exhibiting a preferred embodiment of the present invention. In the figure, the feed line of norbornenes necessary at the initiation of the reaction is omitted. Number 1 means a solvent vessel. It is desirable to employ a solvent having the boiling point of 50–180 degrees centigrade under the ordinary pressure in a preferred embodiment of the invention. The purpose of using solvents lies in the decrease of the concentration for each component in the reaction system, which leads to the reduced generation of heavy-end, that is a byproduct, and especially lies in the prevention of solidification of the circulating 2-norbornenes when they are included in the reaction system (R1=R2=H in the general formula (2)). It is preferred that the boiling point of the used solvent is close to that of 2-norbornenes. In more detail, aromatic and aliphatic hydrocarbons having the carbon number of 6 to 8 are generally preferred.

The hydrocarbon solvents are precisely taken to mean benzene, toluene, xylene, cyclohexane, methylcyclohexane, and dimethylcyclohexane. Among them alicyclic or branched aliphatic hydrocarbons are preferred particularly in view of the safety to the human body and the environment. They include preferably, for example, iso-hexane, iso-heptane, iso-octane, cyclohexane, methylcyclohexane, dimethylcyclohexane, and ethylcyclopentane. Here the compounds like iso-hexane, iso-heptane, and iso-octane are taken to mean hexane, heptane, and octane that possess a hydrocarbon branch or branches larger than or equal to the methyl group. They may be employed regardless of the substituted position or their isomeric form. The preferred concrete examples include 2-methylpentane, 3-methylpentane, 2,3-dimethylbutane, 2-methylhexane, 3-methylhexane, 2,3-dimethylpentane, 2,4-dimethylpentane, 2,2,3-trimethylbutane, 2-methylheptane, 3-methylheptane, 4-methylheptane, 2,3-dimethylhexane, 2,4-dimethylhexane, 2,5-dimethylhexane, 2,2,3-trimethylpentane, 2,2,4-trimethylpentane, 2,3,4-trimethylpentane, and 2,3,3-trimethylpentane. They may be employed regardless of the relative position of substitution for any two methyl-groups. Among these compounds, the alicyclic or branched aliphatic hydrocarbons having the boiling point close to the boiling point of norbornene (95 degrees centigrade) are preferred as mentioned previously. Such solvents may be recovered at distillation safely and simultaneously with norbornenes as a mixture, and thus is preferred for solving the problem of blocking in the lines for recovery and circulation.

In a process employing a solvent and intended to recover 2-norbornenes together with the solvent, it is possible to use water for cooling the distillation condenser (not shown in the figure). Water or seawater may be used. The temperature of the cooling medium is generally set to 0 to 95 degrees centigrade depending on the species and the amount of the solvent. Since the boiling point of 2-norbornenes is 95 degrees, loss of 2-norbornenes into the exhaust gas is worried depending on the distillation pressure. From this viewpoint, the distillation pressure at the top of a distillation tower is preferably set to 10–200 KPa, more preferably to 10–100 KPa, while the preferred temperature of the cooling medium is 0 to 80 degrees, although it depends on the species and the amount of used solvent. Note that solvents and others lost in the exhaust gas at the time of distillation may be substituted to a raw material vessel as a supplement in a proper amount.

In case of using propylene or butene as the olefin (both R1 and R2 are not a hydrogen atom in the general formula (2)), use of solvents is not especially needed as in the case of 2-norbornenes, since alkyl-norbornenes are usually liquid at room temperature. Therefore, in such cases, the solvent vessel is not required in the process flow. Naturally it is still possible to employ a solvent in these occasions. The preferred solvent is one that can be recovered together with the component intended for the circulative re-use in the process, preferably 2-norbornenes or an olefin, more preferably 2-norbornenes. For this reason preferred are solvents having boiling points close to 2-norbornenes, usually solvents having the identical carbon number to 2-norbornenes.

Number 2 in FIG. 1 means a vessel for crude dicyclopentadiene. Under a usual reaction condition described in the present invention, DCPD decomposes to CPD as is shown in the previous equation (1).

Number 3 in FIG. 1 points a vessel for an olefin. More precisely, it is for storing ethylene, propylene, 1-butene, trans-2-butene, or cis-2-butene. The molar ratio of employed olefin to dicyclopentadiene (reducing 2 moles of cyclopentadiene to one mole of dicyclopentadiene) is 0.1–20, preferably 0.2–15, more preferably 0.5–15. At a condition of the above ratio in less than 0.1, norbornenes are generated in an amount smaller than the norbornenes consumed in the production of tetracyclododecenes, making it difficult to circulate a stationary amount in the reaction system. Addition of an olefin in large excess is also not preferred as a large amount of energies are consumed in recovering the olefin.

In the process flow, dicyclopentadiene and/or cyclopentadiene are introduced into the reactor 5 by the transfer pump 4. Olefins (especially ethylene) are first pressured by a pressuring pump (not shown in the flow), and introduced into the reactor 5. The molar feed ratio of alkyl-norbornenes to dicyclopentadiene is 1–50, preferably 1–30, more preferably 1–20. Here the molar amount of supplied cyclopentadiene and/or dicyclopentadiene is calculated based on the molar amount of dicyclopentadiene (for example, 2 moles of cyclopentadiene are equivalent to 1 mole of dicyclopentadiene).

When alkylnorbornenes are employed in the reaction in a large amount, the yield of heavy products becomes comparatively small. But the amount of circulation becomes large, and requires a large amount of energies at distillation, and thus it is not advantageous. When dicyclopentadiene and/or cyclopentadiene are employed in a large amount, the reaction yields heavy products in a large quantity, resulting in the decrease in efficiency for the raw material.

The production reaction of alkyltetracyclododecenes is carried out in the reactor 5 employing the above compounds as the raw material. Any of the complete mixing type or the piston flow type can be employed for the reactor 5. As the commercial product of the piston type reactor, there are Static Mixer made by Noritake Company, Thruzer Mixer made by Sumitomo Heavy Machines, and Sukeya Mixer made by Sakura Industry. The reactor 5 accommodates to the single step type or the multi-step type of more than 2 steps. The complete mixing type reactor and the piston type flow reactor may be employed in parallel or in series.

For the reaction condition at reactor 5, the residence time is set to 0.1–360 minutes, preferably 2–240 minutes. With the residence time less than 0.1 minutes, the reaction yields a large amount of unreacted products, and is not advantageous. The reaction pressure is usually set to 540 MPa, preferably 1–30 MPa. The reaction temperature is usually set to 100–400 degrees centigrade, preferably 150–300 degrees. Especially in case of using dicyclopentadiene as a raw material, the reaction at a temperature higher than 100 degrees causes facile decomposition of dicyclopentadiene to cyclopentadiene, and thus is preferred.

In a method according to the present invention, it is preferred that an olefin of relatively low boiling point is dissolved sufficiently in the liquid phase containing norbornenes, cyclopentadiene and/or dicyclopentadiene. When a solvent is employed in the reaction system, it is preferred that the olefin is dissolved in the solvent sufficiently.

The dissolved state of an olefin depends on the molar mixing ratio of norbornenes, dicyclopentadiene and/or cyclopentadiene, and the olefin. For example, at a ratio of norbornene/dicyclopentadiene/ethylene=8/1/1 with the reaction temperature of 180 degrees, pressures of more than 2.5 MPa are necessary for the dissolution of ethylene. In case of higher ethylene contents and higher temperatures, higher pressures are needed. For example, the reaction at 260 degrees requires roughly a pressure of more than 3.9 MPa.

Use of a solvent facilitates the reaction at low pressures since the dissolution of olefins at lower pressures is feasible. At any rate, the adequate selection of the reaction condition is wanted for obtaining alkyltetracyclododecenes in high yields so that the reaction proceeds in the liquid phase, and the gas phase does not exist substantially within the reactor.

Use of crude DCPD in the reaction according to the present invention induces generation of one, two, or three compounds selected from the group comprising isoprene, piperylene, and 1-methyl-2-norbornene shown by the general formula (4), (hereafter they may be called as isoprene, piperylene, and 1-methyl-2-norbornenes) within the reactor. The generated 1-methyl-2-norbornenes are distilled off together with the circulating norbornenes. The generated isoprene and piperylene are distilled off together with the unreacted CPD and circulated for the re-use. Therefore a considerable part of isoprene, piperylene, and 1-methyl-2-norbornenes generated in the reactor are circulated to the reactor again. When the content of isoprene, piperylene, and 1-methyl-2-norbornene in the raw material increase, that is, when the ratios of isoprene, piperylene, and 1-methyl-2-norbornene against dicyclopentadiene in the raw material increase, the reaction yields increasing byproducts that have boiling points close to that of alkyltetracyclododecenes. Thus it is not preferred.

For the above reason, the reaction according to the present invention is required to maintain the ratios of one, two, or three compounds selected from the group comprising isoprene, piperylene, and 1-methyl-2-norbornene shown by the general formula (4) against the sum of dicyclopentadiene and cyclopentadiene within the specified ranges. All these compounds are contained in the raw material that is fed into the reactor. Here the sum of dicyclopentadiene and cyclopentadiene is taken to mean the summed amount of pure DCPD and pure CPD based on the analysis of gas chromatography, etc. In other words, in a production method according to the present invention, the amount of isoprene is to be maintained within a range of 1–10,000 ppm(wt) against the sum of cyclopentadiene and dicyclopentadiene in the raw material that are introduced into the reactor, preferably 1–7,000 ppm(wt). In a production method according to the present invention, the amount of piperylene is to be maintained within a range of 1–10,000 ppm(wt) against the sum of cyclopentadiene and dicyclopentadiene in the raw material that are introduced into the reactor, preferably 1–7,000 ppm(wt). In a production method according to the present invention, the amount of 1-methyl-2-norbornenes is to be maintained within a range of 1–70,000 ppm(wt) against the sum of cyclopentadiene and dicyclopentadiene in the raw material that are introduced into the reactor, preferably 1–50,000 ppm(wt). These values are defined by the amount per unit time, as they are correlated with the continuous process. When the feed lines to the reactor exist in plural, the above values are defined by the sum of each raw material per unit time. The above amounts of isoprene, piperylene, and 1-methyl-2-norbornenes are to be maintained within the mentioned range in one component only, or in any of two components, or in all three components simultaneously. Preferably they are to be maintained in any two of the three components. When the amounts of isoprene, piperylene, and 1-methyl-2-norbornenes exceed the specified ranges, the reaction yields a quickly increasing amount of byproducts that have the boiling points close to that of alkyltetracyclododecenes, resulting in the diminished purity of the product alkyltetracyclododecenes. Thus it is not preferred. At the same time the reaction by-produces rubber-like polymers of isoprene or piperylene at a section of the distillation towers or the circulation lines inside the reaction system, which causes unwanted problems of blocking, etc.

In the present invention, it is possible to produce highly purified alkyltetracyclododecenes by maintaining the amounts of isoprene, piperylene, and 1-methyl-2-norbornenes within the ranges specified in the above. As these products originate from the impurities existent in the crude DCPD, adjustment of them is feasible through the adjustment of the amount of the crude DCPD fed into the reactor, the amount of circulating norbornenes, and the amount of unreacted CPD. Naturally, they are to be controlled within the specified conditions such as the molar ratio of raw materials and the reaction temperature, etc. Note that the 1-methyl-2-norbornenes shown by the general formula (4) are precisely 1-methyl-2-norbornene when ethylene is used as the olefin shown by the general formula (1).

When propylene or 1-butene is used as the olefin, however, the 1-methyl-2-norbornenes shown by the general formula (4) correspond to 1,5-dimethyl-2-norbornene, 1,6-dimethyl-2-norbornene, 1-methyl-5-ethyl-2-norbornene, or 1-methyl-6-ethyl-2-norbornene, etc.

The reaction mixture discharged continuously out of the reactor is introduced into the distillation process. As in FIG. 1, the reaction mixture coming out of the reactor is introduced into the first distillation tower 6, and adjusted to a pressure of 0.1–1 MPa. Here mainly the unreacted olefin is separated from the top of the tower. The distillation condition is set at will to a pressure within 100–1,000 KPa at the top under a temperature of 25–45 degrees, and a pressure within 100–1,000 KPa at the bottom under a temperature of 25–100 degrees. Pressurization a little higher than the ordinary pressure, especially in case of using ethylene, facilitates the condensation of the top gas by inexpensive seawater or the industrial water.

The unreacted olefin and cyclopentadiene separated from the top of the first distillation tower 6 are recovered, and at least a part of them are circulated to the reactor 5 through the line 11 for the re-use as the raw material. In this occasion light olefins such as ethylene are pressurized on necessity by a pressuring pump (not shown in the figure), and introduced into the reactor. It is also possible to send them to the olefin vessel 3 through the line 11 for the circulation and re-use.

In the process flow, the reaction mixture removed of an olefin and at least a part of cyclopentadiene is discharged from the bottom of the first distillation tower 6, and led into the second distillation tower 7. The distillation condition for the second distillation tower 6 is set to a pressure within 0.1–200 KPa, preferably 1–100 KPa at the top under a temperature of 35–96 degrees, and a pressure within 0.1–200 KPa, preferably 1–100 KPa at the bottom under a temperature of 40–190 degrees.

From the top of the second distillation tower 7, norbornenes, or norbornenes containing a solvent when the solvent is used in the reaction, are separated and recovered. This fraction is circulated to the reactor 5 for the re-use via the line 11. Here the reaction mixture discharged from the bottom of the second distillation tower 7 is set up so as to contain 2-methyl-2-norbornenes shown by the general formula (4). These compounds are difficult to react as is shown in the previous discussion, and also are difficult to decompose.

The distillation condition for the second distillation tower 7 is set to 0.1–200 KPa at its top, preferably 1–100 KPa under a temperature of 35–96 degrees centigrade, and 0.1–200 KPa at its bottom, preferably 1–100 KPa under a temperature of 40–190 degrees. All the distillation towers may be filled up with various fillers in order to raise the distillation efficiency and may be equipped with the refluxing device. The number of theoretical plates in each distillation tower is set to 1–100 plates, preferably 2–50 plates, and more preferably 3–30 plates. The reflux ratio may be determined according to the separation status of each tower, but usually a value of 1–50 is appropriate.

Alkylnorbornenes are discharged from the top of the second distillation tower 7, and at least a part of them are circulated to the reactor 5 through the line 10 for the re-use. This alkylnorbornene fraction contains cyclopentadiene in some cases. When a solvent is employed for the reaction, which partly aims at prevention of solidification of norbornenes, it is preferred to distil off the solvent together with alkylnorbornenes at this position.

The circulating norbornenes alone, or the mixtures of norbornenes and a solvent in case of using the solvent in the reaction, are circulated to the reactor 5 for the re-use via the line 10 to be used again as the raw material. The circulated norbornenes are mixed with the solvent or crude dicyclopentadiene supplied from the solvent vessel 1 or the dicyclopentadiene vessel 2 respectively, conveyed by the liquid transfer pump 4 to the reactor 5.

It is possible to carry out all processes of separating and recovering the unreacted olefin, cyclopentadiene, alkylnorbornenes, as well as a solvent when it is used in the reaction on necessity, in one distillation tower. It is possible to discharge the above fractions simultaneously from the top of a distillation tower, and to circulate at least a part of them to the reactor. The alkylnorbornene fraction discharged from the top of the second distillation tower 7 may be sent to another distillation tower (not shown in the flow) for distillation, and may be extracted of highly purified alkylnorbornenes from the fraction.

The reaction mixture discharged from the bottom of the second distillation tower 7 are sent to the third distillation tower 8, where dicyclopentadiene is separated from its top. The distillation condition is set preferably to 50–120 degrees and less than 30 KPa, to 80–200 degrees and less than 80 KPa for the pressure and temperature at the top and the bottom respectively. The recovered fraction containing dicyclopentadiene may be re-used appropriately as a raw material.

The reaction mixture extracted of dicyclopentadiehe is discharged from the bottom of the third distillation tower 8, and sent to the fourth distillation tower 9. The targeted alkyltetracyclododecenes are extracted from the top of the fourth distillation tower 9, and the heavy products having boiling points higher than those of alkyltetracyclododecenes are discharged from the bottom. The distillation condition is set preferably to less than 200 degrees and less than 30 KPa at its bottom.

As minor impurities contained in the fraction of cyclopentadiene and alkylnorbornenes at the distillation, identified are alkylmethylcyclohexenes, which supposedly come from the reaction of an olefin with isoprene, alkylcyclohexenes coming from the reaction of an olefin with butadiene. Both of the compounds have the boiling points close to those of cyclopentadiene or alkylnorbornenes. In a production method according to the present invention, the addition reaction of an olefin with cyclopentadiene as well as the addition reaction of an olefin with isoprene is confirmed not to occur under the actual reaction condition. Therefore, inclusion of these impurities in the raw materials, which are recovered, circulated, and re-used, does not affect the reaction in any manner.

Addition of appropriate oxidation inhibitors or polymerization inhibitors to the raw material is allowed in this reaction. Preferably added are phenolic compounds such as hydroquinone, 2,6-di-t-butylphenol, 2,6-di-t-butylcresol, 4-methoxyphenol, and hydroxylamines such as N,N-dimethylhydroxylamine or N,N-diethylhydroxylamine. The necessary amount of them against the total raw material fed into the reactor is usually 10–10,000 ppm(wt), preferably 50–5,000 ppm(wt). Addition to the product tetracyclododecenes is also allowable in a range of 50–5,000 ppm(wt).

BRIEF DESCRIPTION OF THE DRAWINGS

FIG. 1 illustrates a process flow for a preferred embodiment of the present invention. In the figure, 1 denotes the vessel for solvent, 2 the vessel for crude dicyclopentadiene, 3 the vessel for an olefin, 4 the liquid transfer pump, 5 the reactor, 6 the first distillation tower, 7 the second distillation tower, 8 the third distillation tower, 9 the fourth distillation tower. Number 10 is the line for recovering and circulating 2-norbornenes, while 11 and 12 are the circulating lines for the unreacted olefin.

BEST MODE FOR CARRYING OUT THE INVENTION

While the invention will be described in detail and with reference to specific examples and comparative examples hereafter, it will be apparent to one skilled in the art that the present invention is not limited in any manner by examples thereof unless they deviate from the purport of the invention.

EXAMPLE 1

A continuous preparation of tetracyclododecenes was carried out employing the equipment in FIG. 1. A mixed raw material comprising norbornenes/methylcyclohexane (solvent) mixed in a ratio of 85/15 was introduced continuously into the reactor 5 together with crude dicyclopentadiene and ethylene for the reaction. The purity for these materials was 99.7 wt % for norbornenes, 73.7 wt % for dicyclopentadiene, and 99.9 wt % for ethylene respectively. The molar ratio of norbornenes/dicyclopentadiene/ethylene was set to 4.5/1/1. The amount of crude dicyclopentadiene was not reduced on the purity, but 132g of crude dicyclopentadiene were assumed to be one mole (this is common to the following examples and comparative examples).

During the reaction, the reactor 5 was kept at a pressure of 5.0 MPa and a temperature of 230 degrees centigrade. The residence time was set to 15 minutes. The reaction mixture discharged from the reactor 5 was introduced into the first distillation tower 6, which had the theoretical number of 20 plates. Its operation at 400 KPa yielded continuously a mixture of ethylene and cyclopentadiene from its top, which was then circulated to the reactor 5 via the line 11.

The reaction mixture discharged from the bottom of the first distillation tower 6 was sent to the second distillation tower 7 having the theoretical number of 30 plates. Norbornenes and methylcyclohexane were recovered there simultaneously under a condition of 43 degrees and 20 KPa at its top position. The content of the recovered liquid was slightly different from the starting composition of norbornenes/methylcyclohexane=85/15. Thus a small portion of methylcyclohexane was added for its correction to the mixture from the vessel I via the line 10, and finally the product was circulated to the reactor 5.

The reaction mixture discharged from the bottom of the second distillation tower 7 was led into the third distillation tower 8 having the theoretical number. of 25 plates, and extracted of the unreacted dicyclopentadiene from its top under a condition of 84 degrees and 10 KPa. The reaction mixture discharged out of the bottom of the third distillation tower 8 was led into the fourth distillation tower 9 having the theoretical number of 25 plates. The product tetracyclododecenes were distilled off from its top under a condition of 89 degrees and 3 KPa. Heavy products having boiling points higher than TCD were recovered from its bottom.

During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 1,100, 10,500, and 71,000 ppm(wt) respectively. These values were stable during the reaction period along with the stable purity of the product tetracyclododecenes in 93.8 wt %. As the result, a stable operation not exhibiting any periodical changes was confirmed.

EXAMPLE 2

The reaction in EXAMPLE 1 was repeated except that the raw material of dicyclopentadiene having the purity of 77.7 wt % was employed.

During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 12,000, 2,000, and 72,000 ppm(wt) respectively. These values were stable during the reaction together with the stable purity of the product tetracyclododecenes in 92.9 wt %. As the result, the stable operation not exhibiting any periodical changes was confirmed.

EXAMPLE 3

The reaction in EXAMPLE 1 was repeated except that the raw material of dicyclopentadiene having the purity of 78.3 wt % was employed.

During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 11,000, 12,000, and 31,000 ppm(wt) respectively. These values were stable during the reaction together with the stable purity of the product tetracyclododecenes in 93.1 wt %. As the result, the stable operation not exhibiting any periodical changes was confirmed.

EXAMPLE 4

The reaction in EXAMPLE 1 was repeated except that a continuous reaction was carried out using norbornenes, dicyclopentadiene, and ethylene in a molar ratio of 8/1/1, operating then the first distillation tower 6 at 200 KPa, disposing the ethylene fraction coming out of the tower, driving the second distillation tower 7 at 30 KPa and 47 degrees at its top, and resulting in the simultaneous recovery of norbornenes and methylcyclohexane.

During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 1,200, 1,100, and 32,000 ppm(wt) respectively. These values were stable during the reaction together with the stable purity of the product tetracyclododecenes in 95.0 wt %. As the result, the stable operation not exhibiting any periodical changes was confirmed.

EXAMPLE 5

The reaction in EXAMPLE 1 was repeated except that a continuous raction was carried out using norbornenes, dicyclopentadiene, and ethylene in a molar ratio of 6.5/1/1. During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 1,100, 1,200, and 72,000 ppm(wt) respectively. These values were stable during the reaction together with the stable purity of the product tetracyclododecenes in 93.5 wt %. As the result, the stable operation not exhibiting any periodical changes was confirmed.

EXAMPLE 6

The reaction in EXAMPLE 1 was repeated except that crude dicyclopentadiene having the purity of 78.3 wt % was employed as a raw material and a continuous reaction was carried out using norbornenes, dicyclopentadiene, and ethylene in a molar ratio of 6.5/1/1. During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 1,300, 12,000, and 40,000 ppm(wt) respectively. These values were stable during the reaction together with the stable purity of the product tetracyclododecenes in 94.1 wt %. As the result, the stable operation not exhibiting any periodical changes was confirmed.

EXAMPLE 7

The reaction in EXAMPLE 1 was repeated except that crude dicyclopentadiene having the purity of 77.7 wt % was employed as a raw material and a continuous reaction was carried out using norbornenes, dicyclopentadiene, and ethylene in a molar ratio of 6.5/1/1. During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 13,000, 1,200, and 38,000 ppm(wt) respectively. These values were stable during the reaction together with the stable purity of the product tetracyclododecenes in 94.7 wt %. As the result, the stable operation not exhibiting any periodical changes was confirmed.

COMPARATIVE EXAMPLE 1

The reaction in EXAMPLE 1 was repeated except that the molar ratio of norbornenes/dicyclopentadiene/ethylene was set to 2/1/1. During a period of continuous operation extending to 200 days, samples were extracted from the reactor periodically at the incoming position of the raw materials, and analyzed for the amounts of isoprene, piperylene, and 1-methyl-2-norbornenes against the sum of pure cyclopentadiene and dicyclopentadiene showing results of 21,000, 23,000, and 95,000 ppm(wt) respectively. The purity of the product tetracyclododecenes was as low as 87.0 wt %. Observation of inside sections of the distillation tower, from which the cyclopentadiene fraction comes out, and the circulating lines after the reaction indicated adhesion of rubber-like substances, which are regarded as polymers of isoprene or piperylene.

EXAMPLE 8

A continuous preparation of tetracyclododecenes was carried out employing the equipment in FIG. 1. Solvents were not employed in this case. A mixed raw material comprising 5-ethyl-2-norbornene/crude dicyclopentadiene/1-butene mixed in a molar ratio of 5/1/7 was introduced continuously into the reactor 5 for the reaction. The purity for these materials was 99.7 wt % for 5-ethyl-2-norbornenes, 73.7 wt % for dicyclopentadiene, and 99.6 wt % for 1-butene respectively.

During the reaction, the reactor 5 was kept at a pressure of 5.0 MPa and a temperature of 230 degrees centigrade. The residence time was set to 30 minutes.

The reaction mixture discharged from the reactor 5 was introduced into the first distillation tower 6, which had the theoretical number of 20 plates. Its operation at 100 KPa yielded continuously 1-butene from its top, which was then circulated to the vessel for butene 3 via the lines 11 and 12 and then to the reactor 5.

The reaction mixture discharged from the bottom of the first distillation tower 6 was sent to the second distillation tower 7 having the theoretical number of 30 plates. And 5-ethyl-2-norbornene were recovered there under a condition of 77–83 degrees and 13 KPa at its top position, and circulated to the reactor 5 via the line 10.

The reaction mixture discharged from the bottom of the second distillation tower 7 was led into the third distillation tower 8 having the theoretical number of 25 plates, and extracted of the unreacted dicyclopentadiene from its top under a condition of 90 degrees and 10 KPa. The reaction. mixture discharged out of the bottom of the third distillation tower 8 was led into the fourth distillation tower 9 having the theoretical number of 25 plates. The product ethyltetracyclododecenes were distilled off from its top under a condition of 118 degrees and 3 KPa. Heavy products having boiling points higher than ethyltetracyclododecenes were recovered from its bottom.

During a period of continuous operation extending to 200 days, samples were extracted from the reactor periodically at the incoming position of the raw materials, and analyzed for the amounts of isoprene, piperylene, and the sum of 6-ethyl-1-methyl-2-norbornene and 5-ethyl-1-methyl-2-norbornene against the sum of pure cyclopentadiene and dicyclopentadiene showing results of 2,000, 1,700 and 43,000 ppm(wt) respectively. These values were stable during the reaction period along with the stable purity of the product ethyltetracyclododecenes in 96.3 wt %. As the result, a stable operation not exhibiting any periodical changes was confirmed.

COMPARATIVE EXAMPLE 2

The reaction in EXAMPLE 8 was repeated except that the molar ratio of 5-ethyl-2-norbornene/dicyclopentadiene/1-butene was set to 2/1/3. During a period of continuous operation extending to 200 days, samples Were extracted from the reactor periodically at the incoming position of the raw materials, and analyzed for the amounts of isoprene, piperylene, and the sum of 6-ethyl-1-methyl-2-norbornene and 5-ethyl-1-methyl-2-norbornene against the sum of pure cyclopentadiene and dicyclopentadiene showing results of 21,000, 27,000, and 83,000 ppm(wt) respectively. The purity of the product ethyltetracyclododecenes was as low as 88.9 wt %. Observation of inside sections of the distillation tower, from which the cyclopentadiene fraction comes out, and the circulating lines after the reaction indicated adhesion of rubber-like substances, which are regarded as polymers of isoprene or piperylene.

EXAMPLE 9

A continuous preparation of methyl-tetracyclododecenes was carried out employing the equipment in FIG. 1. Solvents were no employed in this case. A mixed raw material comprising 5-methyl-2-norbornene/crude dicyclopentadiene/propylene mixed in a ratio of 7/1/6 was introduced continuously into the reactor 5 for the reaction. The purity for these materials was 99.5 wt % for 5-methyl-2-norbornenes, 73.7 wt % for dicyclopentadiene, and 99.5 wt % for propylene respectively.

During the reaction, the reactor 5 was kept at a pressure of 5.0 MPa and a temperature of 230 degrees centigrade. The residence time was set to 30 minutes. The reaction mixture discharged from the reactor 5 was introduced into the first distillation tower 6, which had the theoretical number of 20 plates. Its operation at 150 KPa yielded continuously propylene from its top, which was then circulated to the vessel for propylene 3 via the lines 11 and 12 and then to the reactor 5.

The reaction mixture discharged from the bottom of the first distillation tower 6 was sent to the second distillation tower 7 having the theoretical number of 30 plates. And 5-methyl-2-norbornene were recovered there under a condition of 75–81 degrees and 20 KPa at its top position, and circulated to the reactor 5 via the line 10.

The reaction mixture discharged from the bottom of the second distillation tower 7 was led into the third distillation tower 8 having the theoretical number of 25 plates, and extracted of the unreacted dicyclopentadiene from its top under a condition of 90 degrees and 10 KPa. The reaction mixture discharged out of the bottom of the third distillation tower 8 was led into the fourth distillation tower 9 having the theoretical number of 25 plates. The product methyltetracyclododecenes were distilled off from its top under a condition of 107 degrees and 3 KPa. Heavy products having boiling points higher than methyltetracyclododecene were recovered from its bottom.

During a period of continuous operation extending to 200 days, samples were extracted from the reactor periodically at the incoming position of the raw materials, and analyzed for the amounts of isoprene, piperylene, and the sum of 1,6-dimethyl-2-norbornene and 1,5-dimethyl-2-norbornene against the sum of pure cyclopentadiene and dicyclopentadiene showing results of 1,800, 2,100 and 35,000 ppm(wt) respectively. These values were stable during the reaction period along with the stable purity of the product methyltetracyclododecenes in 95.9 wt %. As the result, a stable operation not exhibiting any periodical changes was confirmed.

COMPARATIVE EXAMPLE 3

The reaction in EXAMPLE 9 was repeated except that the molar ratio of 5-methyl-2-norbornene/dicyclopentadiene/propylene was set to 3/1/2.5. During a period of continuous operation extending to 200 days, samples were extracted from the reactor periodically at the incoming position of the raw materials, and analyzed for the amounts of isoprene, piperylene, and the sum of 1,6-dimethyl-2-norbornene and 1,5-dimethyl-2-norbornene against the sum of pure cyclopentadiene and dicyclopentadiene showing results of 19,000, 21,000, and 81,000 ppm(wt) respectively. The purity of the product methyltetracyclododecenes was as low as 87.8 wt %. Observation of inside sections of the distillation tower, from which the cyclopentadiene fraction comes out, and the circulating lines after the reaction indicated adhesion of rubber-like substances, which are regarded as polymers of isoprene or piperylene.

Industrial Applicability

In the continuous preparation of tetracyclododecenes described in the present invention, it is possible to employ dicyclopentadiene of low purity and crude DCPD as the raw material. It is also possible to maintain a stable, continuous, and longstanding operation for production of highly purified dicyclopentadienes (tetracyclododecenes) by maintaining the ratios of one, two, or three compounds selected from the group comprising isoprene, piperylene, and 1-methyl-2-norbornenes shown by the general formula (4) against the sum of dicyclopentadiene and cyclopentadiene in the raw material that are fed into the reactor within the specified ranges. For these reasons the industrial utility value of the present invention is quite significant.

What is claimed is:

1. A method of continuously preparing tetracyclododecenes comprising

(a) feeding continuously:
  (1) an olefin,
  (2) crude cyclopentadiene, crude dicyclopentadiene, or a mixture thereof and
  (3) norbornenes into a heated reactor, (b) circulating back to said reactor at least a part of norbornenes and cyclopentadiene, distilled out of said reactor, and

(c) maintaining the amounts of one, two, or three compounds selected from the group consisting of,
  isoprene,
  piperylene, and
  1-methyl-2-norbornenes,
  such that
    Isoprene is in the range of 1–10,000 ppm
    Piperylene is in the range of 1–10,000 ppm and
    1-Methyl-2-norbornenes is in the range of 1–70,000 ppm said compounds being compared on a weight basis to the sum of cyclopentadiene and dicyclopentadiene present in the raw materials introduced into the reactor;

wherein said olefin is said norbornene is said tetracyclododecene is and said 1-methyl-2-norbornene is
where R1 and R2 are identical or different functional groups, and are selected from the group consisting of a hydrogen atom, a methyl group, and an ethyl group.

2. A method of continuously preparing tetracyclododecenes comprising:
(a) feeding continuously
(1) an olefin,
(2) crude cyclopentadiene, crude dicyclopentadiene, or a mixture thereof and
(3) norbornenes into a heated reactor,
(b) separating olefin, cyclopentadiene, and norbornenes from the reaction mixture by distillation;
(c) circulating at least a part of olefin, cyclopentadiene, and norbornenes separated in said process of step b to the reactor;
(d) isolating dicyclopentadiene from the reaction mixture by distillation succeeding said process of step b; and
(e) isolating tetracyclododecenes from the reaction mixture by distillation succeeding said process of step d, such that one, two, or three compounds selected from the group consisting of isoprene, piperylene, and 1-methyl-2-norbornenes, are present, wherein
Isoprene is in the range of 1–10,000 ppm,
Piperylene is in the range of 1–10,000 ppm, and
1-Methyl-2-norbornenes is in the range of 1–70,000 ppm said compounds being compared on a weight basis to the sum of cyclopentadiene and dicyclopentadiene present in the raw materials introduced into the reactor;
wherein said olefin is said norbornene is said tetracyclododecene is and said 1-methyl-2-norbornene is and R1 and R2 are identical or different functional groups, and are selected from the group consisting of a hydrogen atom, a methyl group, and an ethyl group.

3. The method of continuously preparing tetracyclododecenes according to claim 1, wherein dicyclopentadiene is distilled off from a distillation tower, the conditions at the top of said tower being in a range of 50–120 degrees and less than 30 KPa, and the reaction conditions at the bottom of said tower being in a range of 80–200 degrees and less than 80 KPa.

4. The method of continuously preparing tetracyclododecenes according to claim 1,
wherein said reaction temperature is in a range of 100–400 degrees, said reaction pressure is in a range of 0.5–40 MPa, and said residence time of said reaction mixture is in a range of 0.1–360 minutes,
and wherein the molar ratios of said olefin and norbornenes, when compared to the sum of dicyclopentadiene and cyclopentadiene present is in a range of 0.1–50 and 1–50 respectively.

5. The method of continuously preparing tetracyclododecenes according to claim 2, wherein said dicyclopentadiene is distilled off from a distillation tower, the conditions at the top of said tower being in a range of 50–120 degrees and less than 30 KPa, the reaction conditions at the bottom of said tower being in a range of 80–200 degrees and less than 80 KPa.

6. The method of continuously preparing tetracyclododecenes according to claim 2,
wherein said reaction temperature is in a range of 100–400 degrees, said reaction pressure is in a range of 0 5–40 MPa, and the residence time of said reaction mixture is in the range of 0.1–360 minutes, and
wherein the molar ratios of said olefin and said norbornenes, when compared to the sum of dicyclopentadiene and cyclopentadiene, present is in a range of 0.1–50 and 1–50 respectively.

* * * * *

UNITED STATES PATENT AND TRADEMARK OFFICE
CERTIFICATE OF CORRECTION

PATENT NO. : 6,441,259 B1
DATED : August 27, 2002
INVENTOR(S) : Fuyuki Aida et al.

It is certified that error appears in the above-identified patent and that said Letters Patent is hereby corrected as shown below:

Column 3,
Line 2, "belolow" should read -- below --;

Column 4,
Line 2, "0.540" should read -- 0.5-40 --;

Column 7,
Line 63, "540" should read -- 5-40 --;

Column 10,
Line 61, "dicyclopentadiehe" should read -- dicyclopentadiene --;

Column 12,
Line 10, "I" should read -- 1 --;

Column 13,
Line 19, "EXAMPLE5" should read -- EXAMPLE 5 --; and

Column 15,
Line 20, "no" should read -- not --.

Signed and Sealed this

Sixteenth Day of December, 2003

JAMES E. ROGAN
*Director of the United States Patent and Trademark Office*